United States Patent [19]

Elliott

[11] Patent Number: 5,034,544
[45] Date of Patent: Jul. 23, 1991

[54] ANTIVIRAL 2,3-BIS-(ARYL)-3-CHLOROPROPENAL COMPOUNDS

[76] Inventor: Irvin W. Elliott, 2014 Jordan Dr., Nashville, Tenn. 37218

[21] Appl. No.: 412,338

[22] Filed: Sep. 26, 1989

[51] Int. Cl.$^5$ .................... C07D 317/52; C07C 47/21
[52] U.S. Cl. .................................. 549/435; 549/436; 568/442
[58] Field of Search ................ 549/435, 446; 568/442

[56] References Cited

U.S. PATENT DOCUMENTS 3,772,297 11/1973 Bartmann et al. .................. 568/442
4,182,730 1/1980 Virgilio et al. ...................... 568/436

Primary Examiner—Nicky Chan
Attorney, Agent, or Firm—Richard C. Litman

[57] ABSTRACT

Novel 2,3-bis-(aryl)-3-chloropropenals corresponding to the formula

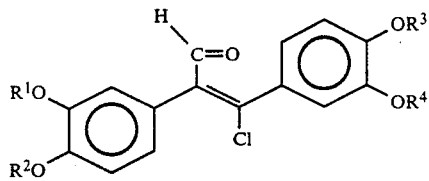

which exhibit activity, pharmaceutical compositions containing the novel compounds as the active component and a method for treatment of virus infections in hosts by administering an effective antiviral amount of the compositions.

3 Claims, 2 Drawing Sheets

ANTIVIRAL 2,3-BIS-(ARYL)-3-CHLOROPROPENAL COMPOUNDS

FIELD AND BACKGROUND OF THE INVENTION

The present invention relates to certain compounds which have useful antiviral activity. More particularly, the invention relates to novel antiviral compounds derived from 2,3-bis-(aryl)-3-chloropropenal derivatives, and antiviral compositions containing these compounds, and to methods of using the compositions to treat viral infections.

Infectious diseases induced by various viruses create important medical and public health problems. The viruses occurring primarily in man are spread mainly by man himself and are found in all parts of the world. The spread of such viruses are limited by inborn resistance, prior immunizing infections or vaccines, sanitary and other public health control measures, and, in a few instances, by chemoprophylactic agents.

Most effective prophylactic measures against virus infections have been the administration of a vaccine. However, in the case of human immunodeficiency virus (referred to as HIV) and herpes simplex virus (referred to as HSV), development of a vaccine is inhibited because of the specific properties of these viruses, namely, carcinogenicity and latent infection of the viruses. The carcinogenic properties of HIV is now well known and has been identified as the secondary cause of certain types of malignancies such as Kaposi's sarcoma. Moreover, the infectiousness of HIV, also referred to the AIDS virus, is difficult to diagnose since physically apparent symptoms do not appear immediately after infection and may take years to develop. If the viral infectiousness remains in the vaccine, there is the possibility of latent infection which may induce serious symptoms to the human body. There is also the possibility that an individual infected with the AIDS virus may develop clinical symptoms of other serious diseases induced by an already damaged immune system. Thus, it would be very difficult to confirm that the infectiousness of HIV was removed in a prepared vaccine and explains why there is presently no vaccine to prevent or treat AIDS. In addition, the vaccine to be used for protection to the herpes simplex infection, which has a low lethal rate, must be highly purified in order to eliminate any undesirable side effects. Accordingly, a safe vaccine for prophylaxis of infection by HSV is presently unavailable for practical use.

Considerable research and resources have recently been devoted to chemotherapeutic measures for treatment of virus infections. In general, most clinically useful antiviral drugs interfere or halt RNA or DNA synthesis. Some drugs have the property of inhibiting maturation processes in the replication cycle of viruses, while others interfere with binding or absorption of viruses to specific host cells or tissues. Still others prevent the uncoating of the viruses following absorption into the cell and some antiviral agents restrict the spread of progeny viruses from cell to cell or from infected tissues to other sites.

Difficulties with antiviral chemotherapy arise because of the obligatory dependence of viruses on host cell metabolism. Also, few virus-specific enzyme systems are as yet vulnerable to chemotherapeutic intervention. Moreover, antiviral agents that block viral replication also block normal host cell processes, and the limits between effective and toxic doses are extremely narrow. Certain of these non-selective agents are usually toxic to both infected and uninfected cells and are not used clinically because of this toxicity. Further, there are numerous complications for clinically useful antiviral agents, including a wide variety of side effects and a relatively low therapeutic index. Patients receiving these agents must be carefully monitored since some resistant virus strains have developed in patients receiving initially effective therapy.

The currently available antiviral agents include idoxuridine (IDU), an anti-herpetic drug which apparently act by being phosphorylated and incorporated into newly synthesized DNA, producing an abnormal and essentially nonfunctional DNA molecule. The drug acts on both viral and host cell DNA and is highly toxic to host cells. Clinical use of IDU has been limited to topical therapy because of its systemic toxicity. Another drug which apparently interferes with viral DNA synthesis and is effective in the treatment of herpes simplex virus infections is adenine arabinoside (Ara-A). Ara-A is useful for prophylaxis of certain infections caused by HSV type 1 and type 2. Adenine arabinoside appears less susceptible to the development of drug resistant viral strains than idoxuridine, and IUD resistant infections often respond to Ara-A treatment.

The AIDS epidemic is driving the current clinical trials that rigorously test an array of promising new drugs which have been shown to be effective in their antiviral properties in cell culture. However, among these many promising drugs that seem effective in slowing the multiplication of the AIDS virus, only azidothymidine, or AZT, has been approved for prescription use by the Food and Drug Administration (FDA). Other experimental drugs which in preliminary studies seems to suppress the production of the AIDS virus is dideoxyinosine (ddI, a less toxic AZT derivative) and interferon, but have yet not won approval by the FDA. Various other promising drugs have not been proved to be efficacious in the treatment of HIV or HSV infections in humans because of their cytotoxicity.

SUMMARY OF THE INVENTION

It is therefore a primary object of the present invention to provide pharmaceutical compositions derived from novel compounds which are useful as antiviral agents.

It is an additional object of the present invention to provide a method for inhibiting the growth of viruses and treating resultant viral infections utilizing novel antiviral compositions.

It is among the additional objects of the invention to provide new 2,3-bis-(aryl)-3-chloropropenal derivatives which have been discovered to possess antiviral activity, are particularly effective as antiviral agents in cell culture against HIV, and are able to treat human immunodeficiency virus infections of hosts.

Accordingly, the present invention provides 2,3-bis-(aryl)-3-chloropropenal derivatives having antiviral activity and corresponding to the following formula:

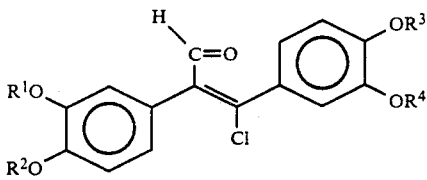

wherein

R[1], R[2], R[3], and R[4] represent a lower alkyl group having 1 to 4 carbon atoms, preferably a methyl group, or where (R[1] and R[2]) and (R[3] and R[4]) may be joined together to form a methylene group (—CH$_2$—).

The present invention is also directed to antiviral compositions containing the above described 2,3-bis-(3,4-disubstituted phenyl)-3-chloropropenal derivatives, and to a method of using these compositions to treat viral infections in hosts. In addition, the invention is directed to novel intermediates useful in preparing the derivatives of the invention.

The above description, as well as further objects, features and aspects of the present invention, will be more fully appreciated by reference to the following detailed description, including the accompanying drawings.

DETAILED DESCRIPTION OF THE INVENTION

Figure 1:
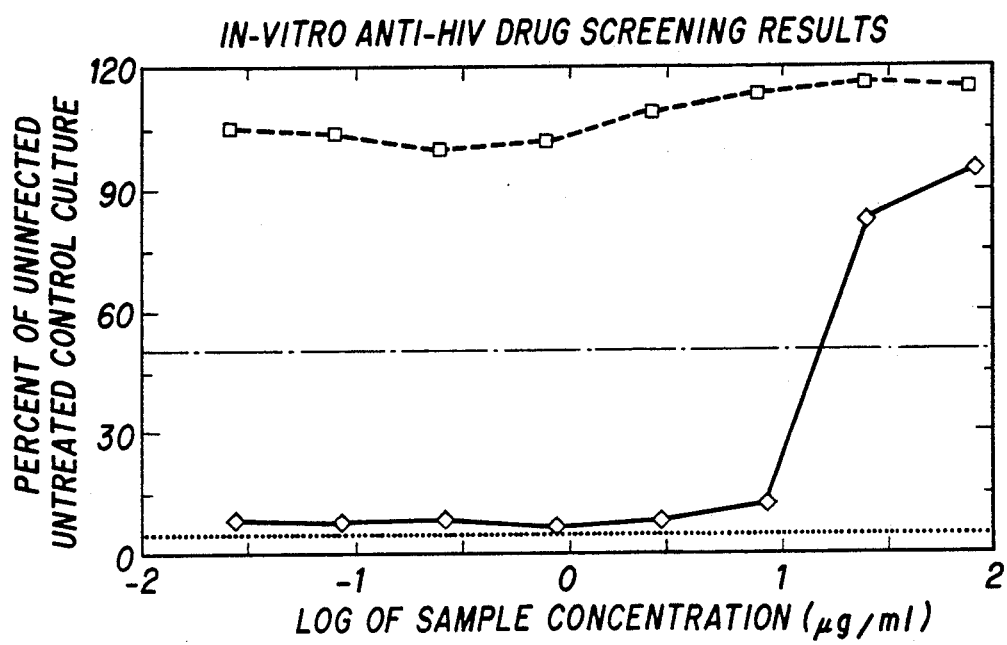
FIGS. 1-4 are graphs which illustrate the effectiveness of the compositions according to present invention against human immunodeficiency virus (HIV).

The compounds of the present invention are synthesized by the converting an aryl benzyl ketone to the desired corresponding 3-chloropropenal via the Vilsmeier reaction as shown below:

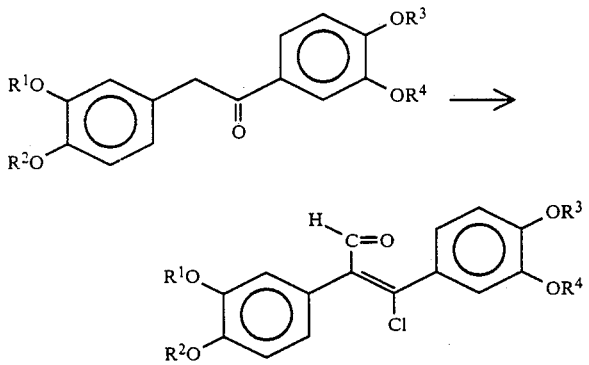

wherein R[1], R[2], R[3] and R[4] have the meaning set forth hereinabove. The Vilsmeier reaction is well-known for formylation of ketones and parallels work disclosed in U.S. Pat. No. 3,772,297 to Bartmann et al. and U.S. Pat. No. 4,182,730 to Virgilio et al. The Vilsmeier reaction is accomplished via Vilsmeier reagents which is the reaction product of a disubstituted amide and an acid chloride. The Vilsmeier reagents employed in the present formylation reaction are prepared by reacting dimethylformamide or methylformanilide with phosphoryl chloride or phosgene. It is preferred to prepare the Vilsmeier reagent with dimethyformamide and phosphorous oxychoride in equivalent amounts.

The preparation of the 3-chloropropenal derivatives of the present invention may be conducted in the absence of a solvent or in the presence of excess dimethylformamide as the solvent. It is preferred, however, that the reaction be carried out in a suitable Friedel Crafts type solvent, such as tetrahydrofuran, to suppress the formation of undesirable cyclic by-products and facilitate the separation of the desired 3-chloropropenal derivatives.

The Vilsmeier reaction is exothermic and it is preferred to add the dimethylforamide-phosphorous oxychloride reaction product to a cooled solution of the aryl benzyl ketone at such a rate as to keep the temperature of the reaction mixture anywhere from 0° C. to about 60° C. It is especially preferred that the temperature of the reaction solution be kept below 30° C.

The reaction time is dependent upon the temperature and reactants used, and can vary from 20 minutes to 24 hours. Most reactions carried out under preferred conditions are usually complete in about two to twelve hours.

The 3-chloropropenal products of the invention are isolated by treating the reaction mixture with a sufficient amount of water to effect hydrolysis of any Vilsmeier intermediates, extracting the crude product formed with a suitable organic solvent and purifying the product by crystallization.

The aryl benzyl ketones used to synthesize the novel 2,3-bis-(3,4-disubstituted phenyl)-3-chloropropenals of the present invention may be available or can be easily prepared via a Friedel Crafts reaction between the appropriate disubstituted phenylacetic acid or acid chloride and disubstituted benzene in excess polyphosphoric acid (PPA) as shown below:

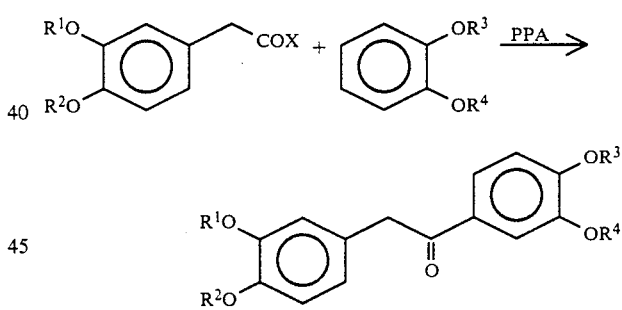

wherein X represents a hydroxy group or chlorine, and R$_1$-R$_4$ have the meanings set forth hereinabove. Alternatively, the prerequisite aryl benzyl ketones can be readily prepared by an aldol condensation of an appropriate disubstituted benzaldehyde in the presence of potassium cyanide (KCN) to form the corresponding benzoin intermediate, which is then reduced by activated zinc.

The novel compounds of the present invention are distinguished by valuable antiviral properties and may be employed in the treatment of viral infections in various hosts. In accordance with the invention, antiviral compositions are provided comprising as the active ingredient an effective amount of the compounds of the invention and a non-toxic pharmaceutical acceptable carrier or diluent. While effective amounts may vary, as conditions in which the antiviral compositions are used vary, the active compounds are generally present at a concentration ranging from 0.5 mg/ml to 100 mg/ml. A minimal dosage required to inactivate the virus is generally between 0.0002 to 20 micrograms (μg) against 25 to 80 plague forming units of virus. The antiviral compositions of the invention are active for inhibiting or inactivating a diverse range of viruses including, but not limited to, vesicular stomatitis virus (VSV), herpes simplex virus 1 and 2 (HSV-1 and HSV-2), cytomegalovirus (CMV) and human immunodeficiency virus (HIV). Examples of suitable pharmaceutical acceptable carriers or diluents include, but not limited to, ethanol, dimethyl sulfoxide and glycerol. The antiviral compositions may be administered in the form of pharmaceutical formulations prepared by any of the methods well known in the art of pharmacy.

In accordance with the invention, a method for inhibiting viruses in a host is provided comprising contacting viruses with an effective amount of the antiviral compositions of the invention. The effectiveness of the compositions of the invention for inhibiting viruses in cell culture systems indicates their usefulness for controlling viruses and virus related diseases in other hosts including mammals.

The compounds of the invention and processes for their synthesis are further described in the following examples. In the examples melting points (mps.) are uncorrected and IR spectra were recorded as paraffin oil mulls. All temperatures are reported in degrees centigrade.

EXAMPLE 1

2,3-Bis-(3,4-Dimethoxyphenyl)-3-Chloropropenal

Desoxyveratroin (2.5 g, 0.0079 moles) was dissolved in a solution of tetrahydrofuran (20 ml) and a preformed solution of dimethylformamide (12 ml) and phophorous oxychloride (7 ml) was added with stirring over a period of 20 minutes to form a reaction mixture. The reaction mixture was kept below 30° by ice bath cooling and stirred for 5 hrs. The resulting slurry was then poured into water (200 ml) and stirred for 18 hrs. The crude product (2.9 g, mp. 162°-166°) was recrystallized from methanol-benzene to yield 1.7 g (59%) of the title compound as yellow needles, mp. 183°-184°. IR(mull): 1665, 1589 cm$^{-1}$; $^{1}$H-NMR (CDCl$_3$): δ3.93 (s, 12H), 7.0 (m, 6H), 9.8 (s, 1H); mass spectrum: M+364 (100%).

EXAMPLE 2

Desoxyveratroin

A warm solution of 3,4-dimethoxyphenylacetic acid (10 g) in veratrole (15 ml) was added to 200 g of polyphosphoric acid (PPA). After 24 hrs. at room temperature the acid mixture was added to cold water (800 ml) and the product was collected and recrystallized from aqueous ethanol. The recrystallized intermediate (9.5 g, 60% yield) had a melting point of 104°-105°.

EXAMPLE 3

2,3-Bis-(3,4-Methylenedioxyphenyl)-3-Chloropropenal

Desoxypiperoin (2.6 g) as reacted in the same manner as Example 1 to yield 1.2 g (40%) of the desired product, mp. 167°-168°. NMR and IR spectral data were consistent with assigned structure.

ANTIVIRAL ACTIVITY

The following experimental tests were utilized to demonstrate the in-vitro antiviral effectiveness of compositions of the present invention. The procedure used in the tests was specifically designed to determine if the present compositions possess antiviral activity against the replication of human immunodeficiency virus (HIV) acting at any stage of the virus reproductive cycle. The assay basically involves the killing of T4 lymphocytes by HIV in cell cultures. Small amounts of HIV are added to cells, and at least two complete cycles of virus reproduction are necessary to obtain the required killing. Agents which interact with virions, cells, or virus gene-products to interfere with viral activities will protect cells from cytolysis. All tests are compared with a positive control done at the same time under identical conditions. The positive control in these experiments was AZT.

Harvest experiments were conducted in which HIV infected cell cultures were post-treated with the compound of Example 1 at a number of concentrations. T4 lymphocytes (CEM cell line) are exposed to HIV at a virus to cell ratio approximately 0.05, and plated along with noninfected control cells in 96-well microtiter plates. 2,3-Bis-(3,4-dimethoxyphenyl)-3-chloropropenal was dissolved in dimethyl sulfoxide, then diluted 1:200 in cell culture medium. Further dilutions (half-log$_{10}$) are prepared before adding to an equal volume of medium containing either infected or noninfected cells. Plates are incubated at 37° C. in a 5% carbon dioxide atmosphere for 6 days. Triphenyl tetrazolium chloride (1% weight by volume) is added to each well and cultures are further incubated to allow color development of viable cells. Individual wells are analyzed spectrophotometrically to quantitate color production and are viewed microscopically for detection of viable cells and confirmation of protective activity. Drug-treated virus-infected cells are compared with drug-treated noninfected cells and other appropriate controls (untreated infected and untreated noninfected cells, drug-containing wells without cells, etc.) on the same plate. Data are reviewed in comparison with other tests done at the same time, and a determination about antiviral activity is made.

FIG. 1 was generated from the above results and graphically displays a plot of the Log 10 of the present composition's concentration (as μg/ml) against the measured test values expressed as a percentage of uninfected, untreated control values. The solid line connecting the diamond symbols depicts the percentage of surviving HIV-infected cells treated with the present test sample at the indicated concentration relative to uninfected, untreated controls. This line represents the in-vitro anti-HIV activity of the sample. The dashed line connecting the square symbols depicts the percentage of surviving uninfected cells treated with the present compound relative to the same uninfected, untreated controls. This line represents the in-vitro growth inhibitory properties. The viral cytopathic effect in this experiment is indicated by a dotted reference line. This line show the extent of destruction of cells by the virus in the absence of treatment and is used as a quality control parameter. Values of this parameter less than 50% are considered acceptable in the current protocol. Reference line at 50% is depicted as alternating dots and dashes.

A listing of the numerical data plotted in the graph of FIG. 1 is provided in Table 1.

TABLE 1

| INFECTED CULTURE | | UNINFECTED CULTURE | |
|---|---|---|---|
| Dose (μg/ml) | Response (%) | Dose (ug/ml) | Response (%) |
| 2.66 × 10$^{-1}$ | 8.2 | 2.66 × 10$^{-2}$ | 104.4 |
| 8.40 × 10$^{-2}$ | 7.5 | 8.40 × 10$^{-2}$ | 103.1 |

TABLE 1-continued

| INFECTED CULTURE | | UNINFECTED CULTURE | |
|---|---|---|---|
| Dose (µg/ml) | Response (%) | Dose (ug/ml) | Response (%) |
| $2.65 \times 10^{-1}$ | 7.8 | $2.65 \times 10^{-1}$ | 99.7 |
| $8.39 \times 10^{-1}$ | 6.1 | $8.39 \times 10^{-1}$ | 101.2 |
| $2.65 \times 10^{+0}$ | 8.0 | $2.65 \times 10^{+0}$ | 108.3 |
| $8.38 \times 10^{+0}$ | 12.2 | $8.38 \times 10^{+0}$ | 113.1 |
| $2.64 \times 10^{+1}$ | 81.6 | $2.64 \times 10^{+1}$ | 115.9 |
| $8.37 \times 10^{+1}$ | 94.2 | $8.37 \times 10^{+1}$ | 114.3 |

From the above results, it is clear that the compound of Example 1, namely 2,3-bis-(3,4-dimethoxyphenyl)-3-chloropropenal, is able to prevent the replication of human immunodeficiency virus in cell culture, therefore establishing it as an antiviral agent. The present compound exhibited significant antiviral activity throughout the range of concentrations and demonstrated an $EC_{50}$ (effective kill concentration for 50% of the experimental virus) of about $1.56 \times 10^{+1}$ µg/ml. An $IC_{50}$ index (inhibition concentration required for 50% of cell growth) of greater than $8.37 \times 10^{+1}$ µg/ml can be clearly observed from the graph of FIG. 1 for the instant compound. The $TI_{50}$ (therapeutic index) for the tested compound was calculated as the ratio of IC:EC and found to be greater than $5.33 \times 10^{+0}$.

Figure 2:
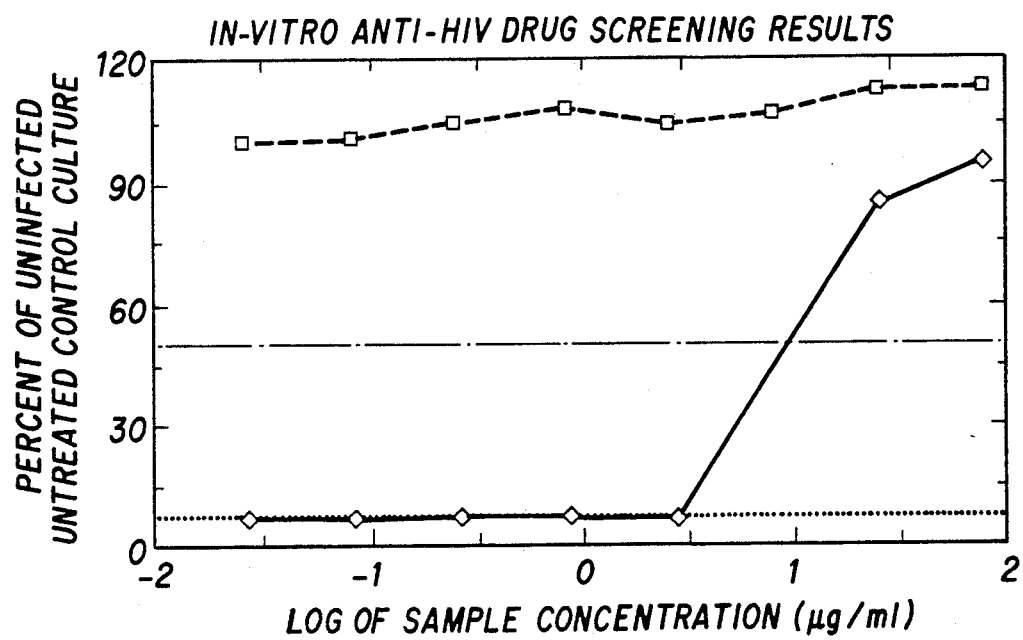
Figure 3:
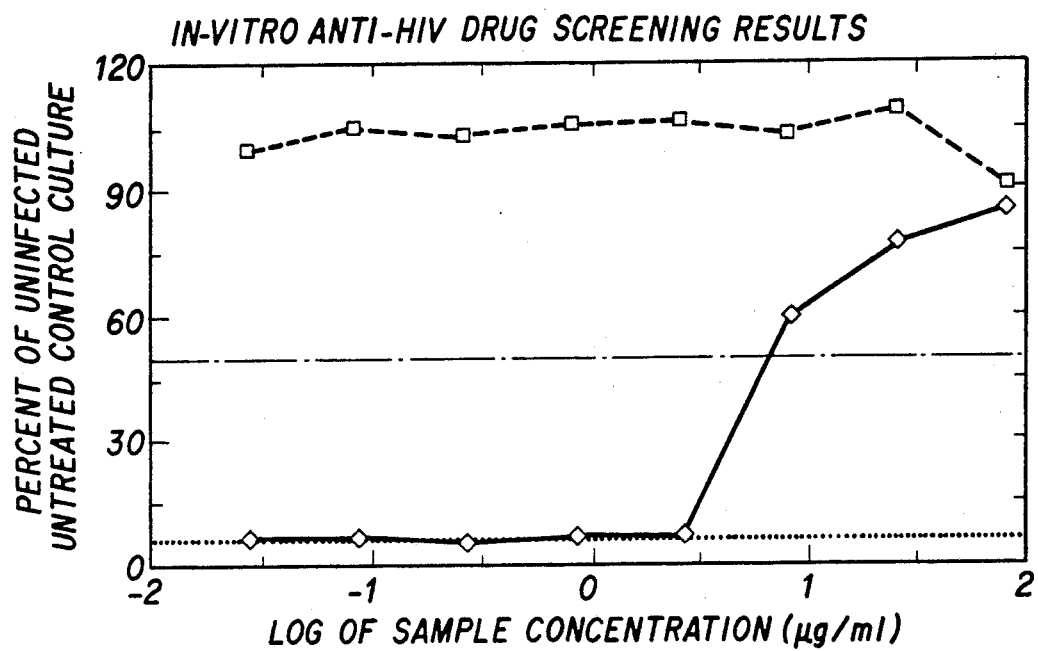
Figure 4:
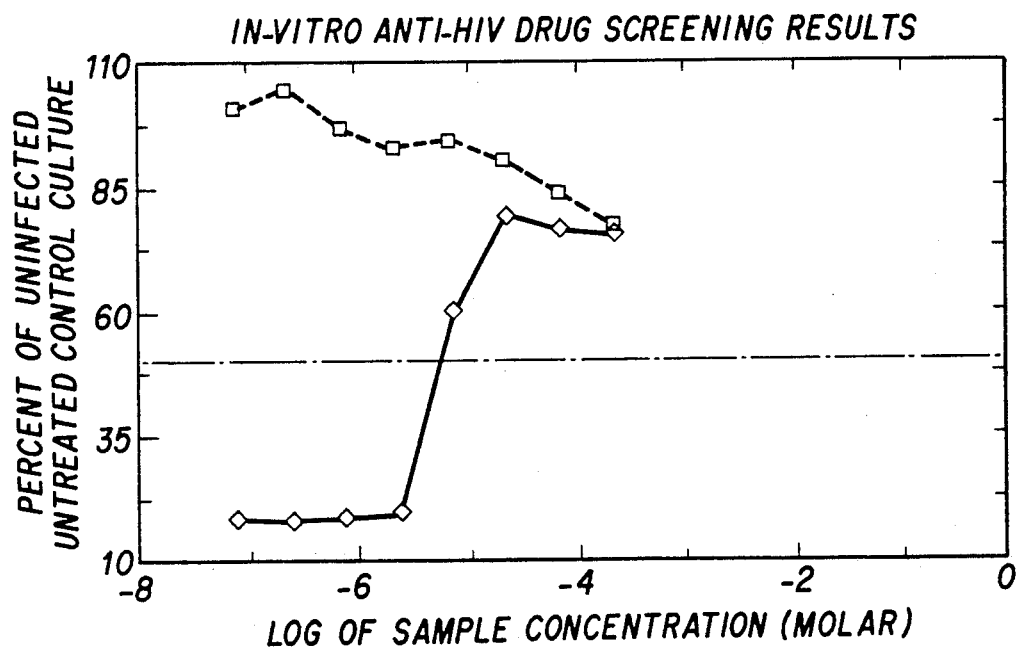

FIGS. 2, 3, and 4 similarly illustrates the effectiveness of 2,3-bis-(3,4-dimethoxyphenyl)-3-chloropropenal against the HIV virus utilizing the assay procedure set forth hereinabove. The results of the tests are set forth in Tables 2, 3, and 4 below which provides reported values plotted in the corresponding graphs of FIGS. 2, 3 and 4, respectively.

TABLE 2

| INFECTED CULTURE | | UNINFECTED CULTURE | |
|---|---|---|---|
| Dose (ug/ml) | Response (%) | Dose (ug/ml) | Response (%) |
| $2.66 \times 10^{-2}$ | 7.3 | $2.66 \times 10^{-2}$ | 99.2 |
| $8.40 \times 10^{-2}$ | 6.5 | $8.40 \times 10^{-2}$ | 99.6 |
| $2.65 \times 10^{-1}$ | 6.9 | $2.65 \times 10^{-1}$ | 103.4 |
| $8.39 \times 10^{-1}$ | 6.8 | $8.39 \times 10^{-1}$ | 107.0 |
| $2.65 \times 10^{+0}$ | 6.6 | $2.65 \times 10^{+0}$ | 103.5 |
| $2.64 \times 10^{+1}$ | 84.6 | $8.38 \times 10^{+0}$ | 106.0 |
| $8.37 \times 10^{+1}$ | 94.8 | $2.64 \times 10^{+1}$ | 112.4 |
| | | $8.37 \times 10^{+1}$ | 112.2 |

TABLE 3

| INFECTED CULTURE | | UNINFECTED CULTURE | |
|---|---|---|---|
| Dose (ug/ml) | Response (%) | Dose (ug/ml) | Response (%) |
| $2.66 \times 10^{-2}$ | 6.9 | $2.66 \times 10^{-2}$ | 99.2 |
| $8.40 \times 10^{-2}$ | 6.8 | $8.40 \times 10^{-2}$ | 104.5 |
| $2.65 \times 10^{-1}$ | 5.4 | $2.65 \times 10^{-1}$ | 102.7 |
| $8.39 \times 10^{-1}$ | 7.2 | $8.39 \times 10^{-1}$ | 105.6 |
| $2.65 \times 10^{+0}$ | 7.0 | $2.65 \times 10^{+0}$ | 106.3 |
| $8.38 \times 10^{+0}$ | 59.7 | $8.38 \times 10^{+0}$ | 103.1 |
| $2.64 \times 10^{+1}$ | 77.5 | $2.64 \times 10^{+1}$ | 109.3 |
| $8.37 \times 10^{+1}$ | 85.3 | $8.37 \times 10^{+1}$ | 91.9 |

TABLE 4

| INFECTED CULTURE | | UNINFECTED CULTURE | |
|---|---|---|---|
| Dose (Molar) | Response (%) | Dose (Molar) | Response (%) |
| $7.33 \times 10^{-8}$ | 18.5 | $7.33 \times 10^{-8}$ | 100.7 |
| $2.31 \times 10^{-7}$ | 18.0 | $2.31 \times 10^{-7}$ | 104.3 |
| $7.32 \times 10^{-7}$ | 18.8 | $7.32 \times 10^{-7}$ | 96.5 |
| $2.31 \times 10^{-6}$ | 19.9 | $2.31 \times 10^{-6}$ | 92.7 |
| $7.31 \times 10^{-6}$ | 60.2 | $7.31 \times 10^{-6}$ | 94.3 |
| $2.31 \times 10^{-5}$ | 79.5 | $2.31 \times 10^{-5}$ | 90.2 |
| $7.30 \times 10^{-5}$ | 76.2 | $7.30 \times 10^{-5}$ | 83.5 |
| $2.30 \times 10^{-4}$ | 75.4 | $2.30 \times 10^{-4}$ | 77.3 |

The cytotoxicity of the test compound may be observed for identical concentrations in identical tests in which the virus was omitted. As summarized in the foregoing tables, no significant visual or microscopic cytotoxicity was observed in the uninfected culture and as the values reported in the above tables indicate, cell growth actually increased in most of these test results. Thus, the foregoing data demonstrate that the instant compound of the invention is selective, exhibiting toxicity to infected cells, yet not toxic towards normal cells or cells free of virus. Also, every attempt was made to reduce variability in the assay procedure set forth hereinabove and the values for $EC_{50}$, $IC_{50}$ and Therapeutic Index (TI) were determined within experimental limitations. However, in the graphic results displayed in FIG. 4 and the tabular dose response data listed in Table 4, the sample's concentration is given in molar amounts rather than micrograms per milliliter (µg/ml). The molar values for $EC_{50}$, $IC_{50}$ and $TI_{50}$ were computed to be $5.45 \times 10^{-6}$, $>2.30 \times 10^{-4}$ and $>4.22 \times 10^{+1}$, respectively, from the graphic results of the experiment depicted in FIG. 4.

The foregoing test data demonstrate the antiviral activity of 2,3-bis-(3,4-dimethoxyphenyl)-3-chloropropenal, which is currently undergoing further preclinical trials. The selectivity of the present compound of the invention, compared to AZT, is pronounced at the reported concentrations. In particular, under the in vitro toxicity conditions reported, AZT exhibited microscopic cytotoxicity to uninfected cells. Also, while 2,3-bis-(3,4-methylenedioxypheny)-3-chloropropenal of the invention produced mixed results under the experimental assay procedure reported hereinabove, the results clearly indicated antiviral activity. However, the spectrum of antiviral activity demonstrated by 2,3-bis-(3,4-methylenedioxyphenyl)-3-chloropropenal was judged to be significantly less than that of the structurally analogous test compound of the invention under the strict experimental conditions reported. Further, a number of structurally related compounds outside the scope of the present invention were tested for antiviral activity according to the anti-HIV drug screen procedure set forth hereinabove. However, none of the analogous compounds tested was rated active under the experimental criteria utilized and the level of activity in all reported incidences were judged to be quantitatively insignificant. One of the compounds tested and found unacceptable for further preclinical consideration was 2,3-di-(4-methoxyphenyl)-3-chloro-acrylaldehyde, disclosed as an intermediate by Bartmann et al in aforementioned U.S. Pat. No. 3,772,297.

The scope of the present invention should not be limited by the examples and suggested uses herein chosen for purposes of disclosure and various changes and modifications can be made without departing from the spirit of the invention. Accordingly, the foregoing illustrations are not to be interpreted as restrictive of the invention beyond that necessitated by the following claims.

I claim:

1. A compound having the formula

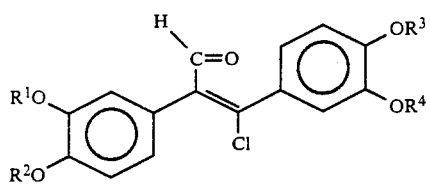
wherein
R[1], R[2], R[3], and R[4] represent a lower alkyl group having 1 to 4 carbon atoms, or where (R[1] and R[2]) and (R[3] and R[4]) may be joined together to form a methylene group.
2. The compound according to claim 1 wherein R[1], R[2], R[3], and R[4] are a methyl group.
3. The compound according to claim 1 wherein (R[1] and R[2]) and (R[3] and R[4]) R[4] are joined together to form a methylene group.
* * * * *